US008940755B2

(12) United States Patent
Tomai et al.

(10) Patent No.: US 8,940,755 B2
(45) Date of Patent: Jan. 27, 2015

(54) THERAPEUTIC COMBINATIONS AND METHODS INCLUDING IRM COMPOUNDS

(75) Inventors: Mark A. Tomai, Woodbury, MN (US); Gary W. Gullikson, Stillwater, MN (US); David M. Hammerbeck, Houlton, WI (US); Elaine A. Egging, Woodbury, MN (US); Michael J. Reiter, New Richmond, WI (US); Christopher D. Gram, River Falls, WI (US); John P. Vasilakos, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1318 days.

(21) Appl. No.: 11/001,979

(22) Filed: Dec. 2, 2004

(65) Prior Publication Data

US 2005/0171072 A1 Aug. 4, 2005

Related U.S. Application Data

(60) Provisional application No. 60/526,240, filed on Dec. 2, 2003.

(51) Int. Cl.
  *A61K 31/56* (2006.01)
  *A61K 31/44* (2006.01)
  *A61K 45/06* (2006.01)
  *A61K 31/00* (2006.01)

(52) U.S. Cl.
  CPC ............... *A61K 45/06* (2013.01); *A61K 31/00* (2013.01)
  USPC ........................... 514/293; 514/171; 514/290

(58) Field of Classification Search
  CPC .................................. A61K 31/00; A61K 45/06
  USPC .......................................... 514/293, 171, 292
  See application file for complete search history.

(56) References Cited

U.S. PATENT DOCUMENTS

| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,376,501 A | 12/1994 | Mariën et al. |
| 5,389,640 A * | 2/1995 | Gerster et al. ............... 514/293 |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,540,931 A | 7/1996 | Hewitt et al. |
| 5,605,899 A | 2/1997 | Gerster et al. |
| 5,693,811 A | 12/1997 | Lindstrom |
| 5,741,908 A | 4/1998 | Gerster et al. |
| 5,756,747 A | 5/1998 | Gerster |
| 5,939,090 A | 8/1999 | Beaurline et al. |
| 5,962,433 A | 10/1999 | Falk et al. |
| 6,028,076 A | 2/2000 | Hirota et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,918 A | 9/2000 | Johnson et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,303,347 B1 | 10/2001 | Johnson et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,451,810 B1 | 9/2002 | Coleman et al. |
| 6,476,000 B1 | 11/2002 | Agrawal |
| 6,518,265 B1 | 2/2003 | Kato et al. |

(Continued)

FOREIGN PATENT DOCUMENTS

| EP | 0 394 026 | 10/1990 |
| EP | 1 104 764 A1 | 6/2001 |

(Continued)

OTHER PUBLICATIONS

Luria et al., Arch. Oediatr Adolesc Med., 2001;155:!340-1345.*
Sangfelt et al., Medical Oncology, 2001;18(1):3-14.*
Smith et al., Dermatologic Surgery, 2001;27(2):143-146.*
Ormond et al., British Journal of Dermatology, 2002;147 (Suppl. 62):57-62.*
Horn et al., Cancer Research, 1981; 41:3155-3160.*
Legha et al., Cancer, 1990;65(11):2478-2481.*

(Continued)

*Primary Examiner* — San-Ming Hui

(74) *Attorney, Agent, or Firm* — Elizabeth S. Capan

(57) ABSTRACT

The present invention provides therapeutic combinations that include an immune response modifier (IRM) component and an anti-inflammatory component. The inventions further provide methods of treating a condition by administering to one having the condition a therapeutic combination that includes an IRM component and an anti-inflammatory component.

13 Claims, No Drawings

(56) References Cited

U.S. PATENT DOCUMENTS

| | | |
|---|---|---|
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,674 B1 | 8/2003 | Schreiber |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,706,728 B2 | 3/2004 | Hedenstrom et al. |
| 6,743,920 B2 | 6/2004 | Lindstrom et al. |
| 6,756,382 B2 | 6/2004 | Rice et al. |
| 6,818,650 B2 | 11/2004 | Griesgraber |
| 2002/0016332 A1 | 2/2002 | Slade |
| 2002/0055517 A1 | 5/2002 | Smith |
| 2002/0110840 A1 | 8/2002 | Tomai et al. |
| 2003/0022302 A1 | 1/2003 | Lewis et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0139441 A1 | 7/2003 | Crooks et al. |
| 2003/0144283 A1 | 7/2003 | Coleman et al. |
| 2003/0161797 A1 | 8/2003 | Miller et al. |
| 2003/0199461 A1 | 10/2003 | Averett et al. |
| 2003/0199538 A1 | 10/2003 | Skwierczynski et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0156849 A1 | 8/2004 | Gurney |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0202720 A1 | 10/2004 | Wightman et al. |
| 2004/0214851 A1 | 10/2004 | Birmachu et al. |

FOREIGN PATENT DOCUMENTS

| | | |
|---|---|---|
| JP | 9-208584 | 8/1997 |
| JP | 11-80156 | 3/1999 |
| JP | 11-222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/059347 A1 | 7/2003 |
| WO | WO 03/086280 | 10/2003 |
| WO | WO 03/089602 | 10/2003 |
| WO | WO 03/094836 | 11/2003 |
| WO | WO 03/094838 | 11/2003 |
| WO | WO 03/097641 A2 | 11/2003 |
| WO | WO 2004/053057 A2 | 6/2004 |

OTHER PUBLICATIONS

Akira et al., "Toll-like receptors: critical proteins linking innate and acquired immunity", *Nature Immunology*, Aug. 2001, vol. 2, No. 8; pp. 675-680.

Akira S. et al., "Recognition of pathogen-associated molecular patterns by TLR family", *Immunology Letters*, 2003, vol. 85, pp. 85-95.

Brassard et al.; "Interferon-α as an immunotherapeutic protein"; Journal of Leukocyte Biology; vol. 71; Apr. 2002; pp. 565-581.

Chollet, et al, "Development of a Topically Active Imiquimod Formulation", *Pharmaceutical Development and Technology*, 4(1), pp. 35-43 (1999).

Edwards, "Imiquimod in clinical practice", *J Am Acad Dermatol*, 2000, vol. 43, pp. 12-17.

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Hemmi et al., "Small anti-viral compounds activate immune cells via the TLR7 MyD88-dependent Signaling pathway", *Nature Immunology*, vol. 3, No. 2; Feb. 2002; pp. 196-200.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", *The Journal of Immunology*, 2002, 168; pp. 4531-4537.

Izumi et al.; "1H-imidazo[4,5-c]quinoline Derivatives as Novel Potent Tnf-α Suppressors: Synthesis and Structure-Activity Relationship of 1-, 2-and 4-Substituted 1H-imidazo[4,5-c]quinolines or 1H-imidazo[4,5-c]pyridines"; *Bioorgianic and Medicinal Chemistry*, vol. 11, pp. 2541-2550 (2003).

Jurk et al. "Human TLR7 and TLR8 independently confer responsiveness to the antiviral. compound R-848", *Nature Immunology*, Jun. 2002, vol. 3, No. 6; p. 1.

Medzhitov, "Toll-Like Receptors and Innate Immunity", *Nature Reviews Immunology*, vol.1; Nov. 2001, pp. 135-145.

Netea et al., "Salmonella septicemia in rheumatoid arthritis patients receiving anti-tumor necrosis factor therapy", *Arthritis & Rheumatism*, Jul. 2003, vol. 48, No. 7, pp. 1853-1857.

Ozinsky A. et al., "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Sauder, "Immunomodulatory and pharmacologic properties of imiquimod", *J Am Acad Dermatol*, 2000, vol. 43, pp. 6-11.

Smith et al., "The imidazoquinolines and their place in the therapy of cutaneous disease", *Expert Opinion*, 2003, vol. 4, No. 7, pp. 1105-1119.

Testerman, et al., "Cytokine Induction by the Immunomodulators Imiquimod and S-27609", *Journal of Leukocyte Biology*, vol. 58, pp. 365-372, Sep. 1995.

Vasilakos, J. P. et al., "Adjuvant Activities of Immune Response Modifier R-848: Comparison with CpG ODN". *Cellular Immunology*. 2000, vol. 204, pp. 64-74.

Wagner, T. L. et al., "Modulation of TH1 and TH2 Cytokine Production with the Immune Response Modifiers, R-848 and Imiquimod". *Cellular Immunology*. 1999, vol. 191, pp. 10-19.

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

Laufer S. et al: "An in-vitro screening assay for the detection of inhibitors of proinflammatory cytokine sythesis: a useful tool for the

(56) References Cited

OTHER PUBLICATIONS development of new antiarthritic and disease modifying drugs" Osteoarthritis and Cartilage, Osteoarthritis Research society, England, vol. 10, No. 12, Dec. 2002, pp. 961-967.

Dockrell et al, "Imiquimod and Resiquimod as Novel Immunomodulators", Journal of Antimicrobial Chemotherapy (2001) 48, 751-755.

* cited by examiner

THERAPEUTIC COMBINATIONS AND METHODS INCLUDING IRM COMPOUNDS

CROSS-REFERENCE TO RELATED APPLICATION

This application claims priority to U.S. Provisional Patent Application Ser. No. 60/526,240, filed Dec. 2, 2003.

BACKGROUND

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis. They may be usefill for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H2$-mediated diseases (e.g., asthma, allergic rhinitis, atopic dermatitis, multiple sclerosis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929) and more are still being discovered. Other IRMs have higher molecular weights, such as oligonucleotides, including CpGs (see, e.g., U.S. Pat. No. 6,194,388).

In view of the great therapeutic potential for IRMs, and despite the important work that has already been done, there is a substantial ongoing need to expand their uses and therapeutic benefits.

SUMMARY

IRM compounds and anti-inflammatory compounds each can be administered to obtain certain therapeutic benefits. It has been found that therapeutic combinations of an IRM compound and an anti-inflammatory compound can provide the therapeutic benefits of treatments that include administering these compounds, but with a reduction in the side effects associated with such treatments.

The therapeutic combinations may provide effective treatment of conditions treatable with an IRM compound while ameliorating side effects associated with IRM therapies. The therapeutic combinations also may provide effective treatment for conditions treatable by administering an anti-inflammatory compound while ameliorating side effects (e.g., immunosuppression) associated with anti-inflammatory therapies.

Accordingly, the present invention provides a therapeutic combination that includes an anti-inflammatory component and an IRM component. The anti-inflammatory component can include one or more of a glucocorticoid, a non-steroidal anti-inflammatory drug, an immunosuppressant, an immunotherapeutic, or any combination thereof. In some embodiments, the IRM component includes a TLR8-selective agonist. In other embodiments, the IRM component includes an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In another aspect, the invention provides a method of treating a condition treatable with an IRM compound. Generally, the method includes administering to a subject having the condition a therapeutic combination that includes an IRM compound in an amount effective to treat the condition; and an anti-inflammatory compound in an amount effective to limit inflammation associated with treating the condition with an IRM compound. In some embodiments, the IRM component includes a TLR8-selective agonist. In other embodiments, the IRM component includes an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In another aspect, the invention provides a method of treating a condition treatable with an anti-inflammatory compound. Generally, the method includes administering to a subject having the condition a therapeutic combination that includes an anti-inflammatory compound in an amount effective to treat the condition; and an IRM compound in an amount effective to limit a side effect associated with treating the condition with the anti-inflammatory compound. In some embodiments, the IRM component includes a TLR8-selective agonist. In other embodiments, the IRM component includes an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Therapies that include administering one or more drugs can result in side effects associated with the therapeutic drug. Side effects can vary in severity and result in, for example, patient discomfort, reduced patient compliance with the therapy, interrupting the therapy, halting the therapy, or even death.

Reducing side effects associated with a therapy can, for example, reduce the likelihood and/or frequency that the therapy must be temporarily or permanently halted due to adverse side effects. Reducing side effects associated with a therapy can, therefore, increase patient compliance, thereby reducing economic costs associated with uncompleted therapy. Reducing side effects associated with a therapy also can, for example, improve the efficacy of a therapy by either promoting completion of the therapy or allowing the therapy to include a greater therapeutic dose for a given tolerable level of therapy side effect. Consequently, methods of limiting the extent to which side effects of a drug therapy negatively influence the outcome of the therapy have substantial medical and economic benefits.

IRM compounds can possess immunostimulating activity including but not limited to antiviral and antitumor activity. Consequently, IRM compounds may be employed in drug therapies designed to treat, for example, viral infections (e.g., genital and perianal warts or Type II Herpes Simplex Virus) and neoplastic tumors (e.g., basal cell carcinoma, actinic keratosis, or melanoma). Side effects associated with certain therapies that include administering certain IRM compounds include signs of inflammation including edema, itching, and pain. While the presence of such signs are, in one respect, an indication that the drug is working as intended (i.e., by stimulating a subject's immune system to clear, for example, a viral infection), individual reactions can vary in severity. Some may desire to decrease such side effects if it is possible to do so and still maintain an effective therapy.

Abnormal regulation of inflammation can give rise to certain inflammatory disorders such as, for example, allergy, asthma, arthritis, including osteoarthritis and rheumatoid arthritis, and autoimmune conditions (e.g., lupus erythematosus). Anti-inflammatory compounds can suppress the immune system, thereby reducing an inflammatory response. Consequently, anti-inflammatory compounds may be used for therapies designed to treat inflammatory disorders by reducing the undesirably high immune activity associated with the inflammatory disorder. While a suppressed immune system can provide relief from the symptoms of an inflammatory disorder, it can also leave one more susceptible to secondary infection or neoplastic diseases, particularly when the anti-inflammatory compound is administered systemically or for a prolonged period. For example, patients taking certain anti-inflammatory compounds (TNF-α inhibitors) are at risk for certain opportunistic infections by, for example, *Mycobacterium tuberculosis, Listeria monocytogenes, Pneumocystis carinii, Aspergillis fumigatus., Candida albicans., Cryptococcus neoformans, Histoplasma capsulatum, Salmonella* spp., or *Coccidioides immitis*. Patients taking TNF-α inhibitors also may be at increased risk for developing certain other conditions including but not limited to pancytopenia and lymphoma.

The present invention provides therapeutic combinations that generally include an IRM compound and an anti-inflammatory compound. Generally speaking, the combination provides a therapeutic effect of one compound—i.e., the compound is provided in an amount effective to treat a condition (a "primary therapy" for treating a primary condition)—and the second compound is provided in an amount effective to ameliorate a side effect of administering the first compound (the "secondary therapy"). In some cases, such as, e.g., opportunistic infections, the secondary therapy may be said to be treating a secondary condition. The secondary nature of the secondary condition refers to the development of the secondary condition as a result of a primary—or prior-occurring—event such as, for example, a primary therapy, and is not intended to reflect the relative severities of the primary and secondary conditions. Therapeutic combinations of the present invention also include combinations that include two or more IRM compounds or two or more anti-inflammatory compounds.

A therapeutic combination may be provided in a single pharmaceutical composition so that both the IRM compound and the anti-inflammatory compound can be administered together. In alternative embodiments, a therapeutic combination may be provided using more than one pharmaceutical composition. In such embodiments, an IRM compound may be provided in one pharmaceutical composition and an anti-inflammatory compound may be provided in a second pharmaceutical composition so that the two compounds can be administered separately such as, for example, at different times, by different routes of administration, and the like. Thus, it also may be possible to provide the IRM compound and the anti-inflammatory compound in different dosing regimens.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

As noted above, certain IRM compounds possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1.

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; and U.S. Patent Publication Nos. 2004/0091491; 2004/0147543; and 2004/0176367.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-β-D-ribofuranosylthiazolo[4,5-d]pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

In some embodiments of the present invention, the IRM compound may include a 2-aminopyridine fused to a five membered nitrogen-containing heterocyclic ring, or a 4-aminopyrimidine fused to a five membered nitrogen-containing heterocyclic ring.

IRM compounds suitable for use in the invention include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound may be an imidazoquinoline amine such as, for example, 1-(2-methylpropyl)-1H-imidazo[4,5-c]quinolin-4-amine, 4-amino-α,α-dimethyl-2-ethoxymethyl-1H-imidazo[4,5-c]quinolin-1-ethanol, 4-amino-α,α-dimethyl-1H-imidazo[4,5-c]quinoline-1-ethanol, or 4-amino-α,α,2-trimethyl-1H-imidazo[4,5-c]quinoline-1-ethanol.

In alternative embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In other alternative embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, a 6-, 7-, 8-, or 9-aryl, heteroaryl, aryloxy or arylalkyleneoxy substituted imidazoquinoline amine, or an imidazoquinoline diamine. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

In certain embodiments, the IRM compound may be sulfonamide substituted imidazoquinoline amine such as, for example, N-[4-(4-amino-2-ethyl-1H-imidazo[4,5-c]quinolin-1-yl)butyl]methanesulfonamide or N-{2-[4-amino-2-(ethoxymethyl)-1H-imidazo[4,5-c]quinolin-1-yl]-1,1-dimethylethyl}methanesulfonamide.

In certain alternative embodiments, the IRM compound may be a tetrahydroimidazoquinoline amine such as, for example, 4-amino-2-(ethoxymethyl)-α,α-dimethyl-6,7,8,9-tetrahydro-1H-imidazo[4,5-c]quinoline-1-ethanol.

In other alternative embodiments, the IRM compound may be an imidazonaphthyridine amine such as, for example, 2-methyl-1-(2-methylpropyl)-1H-imidazo[4,5-c][1,5]naphthyridin-4-amine or N-[4-(4-amino-2-butyl-1H-imidazo[4,5-c][1,5]naphthyridin-1-yl)butyl]-N'-cyclohexylurea.

In still other alternative embodiments, the IRM compound may be a urea substituted tetrahydroimidazoquinoline amine such as, for example, N-[4-(4-amino-2-methyl-6,7,8,9,-tetrahydro-1H-imidazo[4,5-c]quinolin-1-yl)butyl]morpholine-4-carboxamide.

Suitable IRM compounds also may include the purine derivatives, imidazoquinoline amide derivatives, benzimidazole derivatives, adenine derivatives, and oligonucleotide sequences described above.

In some embodiments of the present invention, the IRM compound may be a small molecule immune response modifier (e.g., molecular weight of less than about 1000 Daltons).

In some embodiments of the present invention, the IRM compound may be an agonist of at least one TLR such as, for example, an agonist of TLR6, TLR7, or TLR8. The IRM may also in some cases be an agonist of TLR 9. In certain embodiments, the IRM compound includes a TLR8-selective agonist. In other embodiments, the IRM compound is a TLR7-selective agonist. In still other embodiments, the IRM compound is a TLR7/8 agonist.

As used with respect to the present invention, an agonist of a TLR refers to a compound that, when combined with the TLR, can produce a TLR-mediated cellular response. A compound may be considered an agonist of a TLR regardless of whether the compound can produce a TLR-mediated cellular response by (a) directly binding to the TLR, or (b) combining with the TLR indirectly by, for example, forming a complex with another molecule that directly binds to the TLR, or otherwise resulting in the modification of another compound so that the other compound can directly bind to the TLR. A compound may be identified as an agonist of one or more particular TLRs (e.g., a TLR7 agonist, a TLR8 agonist, or a TLR7/8 agonist).

As used herein, the term "TLR8-selective agonist" refers to any compound that acts as an agonist of TLR8, but does not act as an agonist of TLR7. A "TLR7-selective agonist" refers to a compound that acts as an agonist of TLR7, but does not act as an agonist of TLR8. A "TLR7/8 agonist" refers to a compound that acts as an agonist of both TLR7 and TLR8.

A TLR8-selective agonist or a TLR7-selective agonist may act as an agonist for the indicated TLR and one or more of TLR1, TLR2, TLR3, TLR4, TLR5, TLR6, TLR9, or TLR10.

Accordingly, while "TLR8-selective agonist" may refer to a compound that acts as an agonist for TLR8 and for no other TLR, it may alternatively refer to a compound that acts as an agonist of TLR8 and, for example, TLR6. Similarly, "TLR7-selective agonist" may refer to a compound that acts as an agonist for TLR7 and for no other TLR, but it may alternatively refer to a compound that acts as an agonist of TLR7 and, for example, TLR6.

The TLR agonism for a particular compound may be assessed in any suitable manner. For example, assays for detecting TLR agonism of test compounds are described, for example, in U.S. Patent Publication No. U.S. 2004/0132079, and recombinant cell lines suitable for use in such assays are described, for example, in International Patent Publication No. WO 04/053057.

Regardless of the particular assay employed, a compound can be identified as an agonist of a particular TLR if performing the assay with a compound results in at least a threshold increase of some biological activity mediated by the particular TLR. Conversely, a compound may be identified as not acting as an agonist of a specified TLR if, when used to perform an assay designed to detect biological activity mediated by the specified TLR, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

The precise threshold increase of TLR-mediated biological activity for determining whether a particular compound is or is not an agonist of a particular TLR in a given assay may vary according to factors known in the art including but not limited to the biological activity observed as the endpoint of the assay, the method used to measure or detect the endpoint of the assay, the signal-to-noise ratio of the assay, the precision of the assay, and whether the same assay is being used to determine the agonism of a compound for both TLRs. Accordingly it is not practical to set forth generally the threshold increase of TLR-mediated biological activity required to identify a compound as being an agonist or a non-agonist of a particular TLR for all possible assays. Those of ordinary skill in the art, however, can readily determine the appropriate threshold with due consideration of such factors.

Assays employing HEK293 cells transfected with an expressible TLR structural gene may use a threshold of, for example, at least a three-fold increase in a TLR-mediated biological activity (e.g., NFκB activation) when the compound is provided at a concentration of, for example, from about 1 µM to about 10 µM for identifying a compound as an agonist of the TLR transfected into the cell. However, different thresholds and/or different concentration ranges may be suitable in certain circumstances. Also, different thresholds may be appropriate for different assays.

Suitable anti-inflammatory compounds include compounds that possess anti-inflammatory activity such as, for example, glucocorticoids, non-steroidal anti-inflammatory drugs (NSAIDs), immunosuppressants, and immunotherapeutics (i.e., antibodies). In some embodiments, the anti-inflammatory compound can act as an inhibitor of one or more pro-inflammatory biological mediators (e.g., a cytokine or enzyme) such as, for example, TNF-α, IL-1, IL-2, IL-6, IL-8, IL-12, MIP1-α, MCP-1, COX-2, or NFκB.

Suitable glucocorticoids include, for example, alclometasone, amcidonide, beclomethasone, betamethasone, budesonide, ciclesonide, clobetasol, clobetasone, corticosterone, cortisone, deflazacort, desonide, desoximetasone, dexamethasone, diflucotolone, diflorasone, flumethasone, flunisolide, fluocinolone, fluocinonide, fluocortolone, fluorometholone, flurandrenolone, flurandrenolide, fluticasone, halcinonide, halobetasol, hydrocortisone, methylprednisolone, mometasone, paramethasone, prednisolone, and triamcinolone.

Suitable NSAIDs include, for example, aceclofenac, acemetacin, aminopyrine, azapropazone, benzydamine, bromfenac, bufexamac, carprofen, cinnoxicam, dexketoprofen, diclofenac, diflunisal, dipyrone, etodolac, felbinac, fenbufen, fenoprofen, fentiazac, flufenamic acid, flurbiprofen, ibuprofen, indobufen, indomethacin, indoprofen, ketoprofen, meclofenamate, mefenamic acid, meloxicam, nabumetone, naproxen, niflumic acid, nimesulide, oxaprozin, oxyphenbutazone, phenylbutazone, piroxicam, salicylates (e.g., acetylated salicylates—aspirin—and nonacetylated salicylates), sulindac, suprofen, tenoxicam, tiaprofenic acid, tolfenamic acid, and tolmetin.

Suitable immunosuppressants include, for example, acetretin, alefacept, anakinra, analgesics (e.g., acetaminophen), auranofin, azathioprine, cyclophosphamide, cyclosporin, etanercept, fexofenadine, isotretinoin, leflunomide, methotrexate, minocycline, montelukast, mycophenalate, penicillamine, pimecrolimus, rosiglitazone, sirolimus, sulfasalazine, tacrolimus, tazarotene, verteporfin, zafirlukast, and zileuton.

Suitable immunotherapeutics (e.g., antibodies) include but are not limited to adalimumab, efalizumab, infliximab, omalizumab, mepolizumab, and antibodies directed against any proinflammatory molecule such as, for example, anti-TNF, anti-IL-1, anti-IL-8, or anti-IL-12 antibodies.

In one aspect, the invention provides a therapeutic combination that includes an IRM compound and an anti-inflammatory compound. In certain embodiments, the anti-inflammatory compound can include a glucocorticoid, an immunosuppressant, or an immunotherapeutic, or some combination thereof. In one embodiment, the therapeutic combination includes an IRM compound and a glucocorticoid. In an alternative embodiment, the therapeutic combination includes an immunosuppressant. In yet another alternative, the therapeutic combination includes an immunotherapeutic.

Such a therapeutic combination may be useful, for example, for reducing the extent of inflammation associated with treatments that include administering an IRM compound. For example, Tables 2 and 3 show dose dependent reductions in the synthesis of the pro-inflammatory cytokine tumor necrosis factor alpha (TNF-α) by human peripheral blood mononuclear cells (PBMCs) in response to treatment of the PBMCs with various combinations of an IRM compound and dexamethasone, a glucocorticoid anti-inflammatory compound.

The therapeutic combinations shown in Tables 2 and 3 employ the glucocorticoid in varying concentrations, and the various combinations reduce the synthesis of TNF-α in a dose-dependent manner. Thus, it may be possible to tailor the therapeutic combination to achieve a desired reduction in inflammation by varying the concentration of the glucocorticoid. Also, it may be possible to achieve a desired reduction in inflammation by using one or more alternative glucocorticoids, an immunosuppressant, or an immunotherapeutic.

Each therapeutic combination shown in Table 1 includes the IRM compound 4-amino-α,α-dimethyl-2-ethoxymethyl-1H-imidazo[4,5-c]quinolin-1-ethanol, a known TLR7/8 agonist. However, other embodiments of the invention can include a different TLR7/8 agonist, a TLR7-selective agonist, a TLR8-selective agonist, a TLR9 agonist, or any combination of two or more of the foregoing.

Such a therapeutic combination also may be useful, for example, for limiting one or more side effects that may be experienced by patients undergoing therapy designed to inhibit inflammation such as, for example, anti-TNF therapy. In some cases, the therapeutic combination may improve the efficacy of the therapy by, for example, (1) allowing the patient to tolerate a higher and, presumably, more efficacious dose of the anti-inflammatory compound, (2) providing a positive therapeutic interaction between the IRM compound and the anti-inflammatory compound, or both.

In some embodiments, the therapeutic combination can be employed to limit immunosuppression that may be experienced by subjects undergoing therapy designed to inhibit inflammation such as, for example, anti-TNF therapy. As used herein, limiting immunosuppression can refer to any desired restoration of immune function in a subject receiving a therapeutic combination of the invention compared to one receiving only anti-inflammation treatment. In some embodiments, limiting immunosuppression may manifest as reducing the likelihood or extent of a secondary condition (e.g., opportunistic infection, malignancy, or pancytopenia), or the severity of symptoms associated with a secondary condition.

Therapy designed to inhibit inflammation may be employed to treat inflammatory disorders such as, for example, rheumatoid arthritis, atopic dermatitis, asthma, allergy, and the like. Such therapy can include administering an anti-inflammatory compound (e.g., a TNF inhibitor) systemically that, in addition to suppressing the abnormal immune response that causes the condition for which the therapy was initiated, can suppress the normal immune response that would otherwise protect the patient from certain infections.

Local (i.e., non-systemic) administration of an IRM compound can provide localized immunostimulation to decrease the likelihood and extent of local opportunistic infections, or reduce the severity of opportunistic infections of, for example, the skin (e.g., atypical mycobacterial infections, *Staphylococcus aureus*) or lungs (e.g., atypical mycobacterial infections and opportunistic mycotic infections by, for example, *Aspergillis* spp., *Candida* spp., and *Coccidioides* spp.).

Local administration of certain IRM compounds (e.g., TLR8 agonists) can provide a localized induction of, for example, TNF-α that can promote a localized immune response to prophylactically or therapeutically treat an opportunistic infection without generally interfering with the effectiveness of systemic anti-inflammatory (e.g., anti-TNF) therapy.

Systemic administration of certain IRM compounds can provide systemic immunostimulation to decrease the likelihood or extent of systemic opportunistic infections, or decrease the likelihood or severity of non-infectious disorders such as, for example, certain lymphomas and pancytopenia. For example, certain IRM compounds can selectively induce production and secretion of Type I interferons (e.g., IFN-α), while inducing little or no production and secretion of TNF-α. Thus, the therapeutic combination can provide a therapeutic level of anti-TNF activity, while inducing IFN-α-mediated immunostimulation to reduce the immunosuppression associated with the anti-TNF therapy when it is not provided in combination with an IRM compound.

As another example, a therapeutic combination of the invention may be used to limit the likelihood, extent, or severity of other side effects associated with therapies designed to inhibit inflammation. For example, certain IRMs may be used to limit the likelihood, frequency, and/or severity of nausea or emesis associated with such therapies.

In some embodiments, the therapeutic combination can be used to improve the efficacy of treatment for a $T_H2$-mediated inflammatory disorder. The anti-inflammatory compound may be employed to reduce a $T_H2$ immune response associated with an inflammatory disorder. The IRM compound may be provided to convert the underlying immune response away from a $T_H2$ response toward either a $T_H1$ or a $T_H3$ immune response. Causative antigens associated with the inflammatory disorder will induce less of a $T_H2$ immune response (that which mediates the disorder) and more of a $T_H1$ or $T_H3$ immune response (those that do not mediate the disorder). The resulting improvement of the efficacy of the treatment may be in addition to, or in lieu of, the activity of limiting a side effect of the anti-inflammatory compound. Consequently, the improved efficacy of a treatment for a $T_H2$-mediated inflammatory disorder is the result of a positive therapeutic interaction between the IRM compound and the anti-inflammatory compound, and is not merely due to the patient being able to tolerate—and therefore administering to the patient—a higher dose of the anti-inflammatory compound when provided in combination with an IRM compound.

The IRM compound included in a particular therapeutic combination may vary depending upon, for example, the nature (local opportunistic infection, systemic opportunistic infection, or non-infectious) of the secondary condition sought to be controlled by the IRM compound. In some embodiments, the IRM compound may be a TLR7/8 agonist. In alternative embodiments, the IRM compound may be a TLR7-selective agonist. In additional alternative embodiments, the IRM compound may be a TLR8-selective agonist. In still other embodiments, the IRM compound may be an agonist of TLR9. A therapeutic combination of the invention may, alternatively, include two or more IRM compounds having any combination of desired TLR agonism activity (e.g., a TLR8-selective agonist and a TLR9 agonist).

The anti-inflammatory compound can be any glucocorticoid, NSAID, immunosuppressant, or immunotherapeutic anti-inflammatory compound. For embodiments in which an anti-inflammatory disorder is the primary condition to be treated using the therapeutic combination, the anti-inflammatory compound may be any anti-inflammatory suitable for treatment of the inflammatory disorder. In certain embodiments, the anti-inflammatory compound can include a glucocorticoid. In an alternative embodiment, the anti-inflammatory compound can include an immunosuppressant (e.g., etanercept). In another alternative embodiment, the anti-inflammatory compound can include an immunotherapeutic (e.g., adalimumab, infliximab, or anti-TNF antibodies). A therapeutic combination of the invention may, alternatively, include two or more anti-inflammatory compounds.

Regardless of the particular embodiment, the therapeutic combination may be provided in a single formulation that includes both the IRM compound and the anti-inflammatory compound. Alternatively, the therapeutic combination may include a plurality of formulations. When the combination is provided in a plurality of formulations, the IRM compound and the anti-inflammatory compound may be provided in the same formulation or in different formulations. Formulations suitable for use in connection with therapeutic combinations of the invention are described in detail below.

In another embodiment, the invention includes a therapeutic combination that includes a TLR8-selective agonist and an anti-inflammatory compound. Such combinations may be useful, for example, for reducing the extent of inflammation associated with administering the TLR8-selective agonist. The anti-inflammatory compound may be any suitable anti-inflammatory compound including, for example, a glucocorticoid, an NSAID, an immunosuppressant, or an immunotherapeutic.

The therapeutic combination may be provided in a single formulation that includes both the TLR8-selective agonist and the anti-inflammatory compound. Alternatively, the therapeutic combination may include a plurality of formulations. When the combination is provided in a plurality of formulations, the TLR8-selective agonist and the anti-inflammatory compound may be provided in the same formulation or in different formulations. Formulations suitable for use in connection with therapeutic combinations of the invention are described in detail below.

The therapeutic combination may be provided in any formulation or combination of formulations suitable for administration to a subject. Suitable types of formulations are described, for example, in U.S. Pat. No. 5,736,553; U.S. Pat. No. 5,238,944; U.S. Pat. No. 5,939,090; U.S. Pat. No. 6,365,166; U.S. Pat. No. 6,245,776; U.S. Pat. No. 6,486,186; European Patent No. EP 0 394 026; and International Patent Publication No. WO 03/045391. Each component of the combination may be provided in any suitable form including but not limited to a solution, a suspension, an emulsion, or any form of mixture. As noted above, each component of the combination may be provided together or in separate formulations. Each component of the combination may be delivered in formulation with any pharmaceutically acceptable excipient, carrier, or vehicle. For example, a formulation may be delivered in a conventional dosage form such as, for example, a cream, an ointment, an aerosol formulation, a non-aerosol spray, a gel, a lotion, a tablet, an elixir, and the like. The formulation may further include one or more additives including but not limited to adjuvants, skin penetration enhancers, colorants, flavorings, fragrances, moisturizers, thickeners, and the like.

A formulation containing one or more components of the combination may be administered in any suitable manner such as, for example, non-parenterally or parenterally. As used herein, non-parenterally refers to administration through the digestive tract, including by oral ingestion. Parenterally refers to administration other than through the digestive tract such as, for example, intravenously, intramuscularly, transdermally, subcutaneously, transmucosally (e.g., by inhalation), or topically.

The amount of IRM compound and anti-inflammatory compound provided in a therapeutic combination of the invention may depend, at least in part, on whether the particular compound is being provided as a primary therapy or as a secondary therapy. Generally, the amount of compound effective to provide a primary therapy is not substantially different than the amount of compound effective to provide therapy for the primary condition outside of a therapeutic combination of the invention. In some cases, however, the amount of compound effective for treating a primary condition (i.e., for providing a primary therapy) may differ somewhat from the amount effective to treat the condition in the absence of the secondary component of the therapeutic combination.

For example, in some embodiments, the amount of compound effective to provide the primary treatment may decrease somewhat because of a positive therapeutic interaction between the primary component and the secondary component. As another example, the amount of compound effective to provide the primary treatment may increase somewhat if the secondary component acts as an antagonist of the primary component. In such cases, the secondary therapy provides sufficient benefit to offset any increase in side effects that result from increasing the amount of the primary component compound effective to provide the primary treatment.

In some embodiments, the amount of compound effective for providing the primary therapy may not necessarily change, but a higher dose may be possible because the secondary therapy provided by the secondary component of the combination permits a patient to tolerate the higher dose.

An amount of an IRM compound effective, as a secondary component of a therapeutic combination, for limiting a side effect of a primary therapy is an amount effective to reduce the likelihood, extent, or severity of the side effect (e.g., nausea, immunosuppression, etc.). For example, an amount effective for limiting nausea may be an amount effective, for example, for reducing the likelihood that a patient feels nauseous, the severity of such feelings, or reducing the frequency of, for example, vomiting. As another example, an amount effective for limiting immunosuppression may be an amount sufficient to reduce, for example, the likelihood or extent of a secondary condition, or the severity of symptoms associated with a secondary condition.

The precise amount of IRM compound for limiting a side effect in a particular therapeutic combination of the invention may vary according to factors known in the art such as, for example, the physical and chemical nature of the IRM compound; the nature of the carrier; the particular anti-inflammatory therapy with which the IRM compound is combined; the intended dosing regimen; the extent to which the subject's immune system is suppressed by the anti-inflammation therapy; the method of administering the IRM compound; whether the subject is at risk for any particular secondary condition and, if so, the identity of such a secondary condition; and the species to which the formulation is being administered. Accordingly, it is not practical to set forth generally the amount that constitutes an amount of IRM compound effective for limiting immunosuppression for all possible applications. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the methods may be performed by administering IRM compound in concentrations outside this range. In some of these embodiments, the method includes administering sufficient IRM compound to provide a dose of from about 10 µg/kg to about 5 mg/kg to the subject, for example, a dose of from about 100 µg/kg to about 1 mg/kg.

The IRM compound may be administered to a subject in a formulation that includes, for example, from about 0.001% to about 10% IRM compound (unless otherwise indicated, all percentages provided herein are weight/weight with respect to the total formulation) to the subject, although in some embodiments the IRM compound may be administered using a formulation that provides IRM compound in a concentration outside of this range. In certain embodiments, the method includes administering to a subject a formulation that includes from about 0.01% to about 1% IRM compound, for example, a formulation that includes from about 0.1% to about 0.5% IRM compound.

An amount of an anti-inflammatory compound effective, as a secondary component of a therapeutic combination, for limiting a side effect of a primary therapy is an amount effective to reduce the likelihood, extent, or severity of the side effect (e.g., edema, itching, pain, etc.). For example, an amount of an anti-inflammatory compound effective for reducing, for example, inflammation associated with administering an IRM compound may be an amount sufficient to reduce the likelihood or extent of inflammation in a subject receiving a therapeutic combination of the invention compared to receiving only the IRM compound.

The precise amount of anti-inflammatory compound for limiting a side effect (e.g., reducing inflammation) in a particular therapeutic combination of the invention may vary according to factors known in the art such as, for example, the physical and chemical nature of the anti-inflammatory compound; the potency of the anti-inflammatory compound; the nature of the carrier; the particular IRM compound with which the anti-inflammatory compound is combined; the intended dosing regimen; the nature of the subject's immune system (e.g., suppressed, compromised, stimulated); the method of administering the anti-inflammatory compound; and the species to which the formulation is being administered. Accordingly, it is not practical to set forth generally the amount that constitutes an amount of anti-inflammatory compound effective for limiting immunosuppression for all possible applications. Those of ordinary skill in the art, however, can readily determine the appropriate amount with due consideration of such factors.

In some embodiments, the methods of the present invention include administering sufficient anti-inflammatory compound to provide a dose of, for example, from about 100 ng/kg to about 50 mg/kg to the subject, although in some embodiments the methods may be performed by administering anti-inflammatory compound in concentrations outside this range. In some of these embodiments, the method includes administering sufficient anti-inflammatory compound to provide a dose of from about 10 µg/kg to about 10 mg/kg to the subject. In certain embodiments, the method includes administering sufficient anti-inflammatory compound to provide a dose of from about 50 µg/kg to about 2.5 mg/kg, for example, a dose of from about 200 µg/kg to about 1 mg/kg.

The anti-inflammatory compound may be administered to a subject in a formulation that includes, for example, from about 0.001% to about 10% anti-inflammatory compound to the subject, although in some embodiments the anti-inflammatory compound may be administered using a formulation that provides the compound in a concentration outside of this range. In some embodiments, the method includes administering to a subject a formulation that includes from about 0.01% to about 2.5% anti-inflammatory compound. In certain embodiments, the method includes administering to a subject a formulation that includes from about 0.05% to about 1.0% anti-inflammatory compound, for example, a formulation that includes from about 0.1% to about 0.5% anti-inflammatory compound.

The dosing regimen of each component of a therapeutic combination of the invention may be the same as, or different than, the dosing regimen of the other component. Specifically, the dosing regimen of a component may be dependent upon whether a particular component is providing a primary therapy (i.e., the primary component) or is intended to reduce or limit a side effect associated with the primary therapy (i.e., the secondary component). In either case, the dosing regimen for a compound may depend at least in part on many factors known in the art such as, for example, the physical and chemical nature of the compound, the chemical and physical nature of the other compound of the therapeutic combination, the nature of the carrier, the amount of the other compound of the therapeutic combination being administered, the state of the subject's immune system (e.g., suppressed, compromised, stimulated), and the method of administering the compound, the presence and extent of any interactions between the compound of the primary component and the compound of the secondary component, and the species to which the formulation is being administered.

For the primary component of the therapeutic combination, additional factors include, for example, the typical dosing regimen for the compound used to treat the primary condition.

For the secondary component of the therapeutic combination, additional factors include, for example, the severity of side effect associated with the primary therapy.

Accordingly it is not practical to set forth generally the dosing regimen for each component for all possible therapeutic combinations of the invention. Those of ordinary skill in the art, however, can readily determine the appropriate dosing regimen with due consideration of such factors.

In some embodiments of the invention, the secondary component compound may be administered, for example, from once to multiple times per day. For example, the secondary component compound may be administered from about once per week to about four times per day, although in some embodiments the methods of the present invention may be performed by administering the secondary component compound at a frequency outside this range. In certain embodiments, the secondary component compound is administered from about three times per week to about twice per day. In one particular embodiment, the secondary component compound may be administered on an "as needed" basis. In an alternative embodiment, the secondary component may be administered once per day for three days per week. In an alternative embodiment, the secondary component compound may be administered once per day for four days per week. In another alternative embodiment, the secondary component compound may be administered once per day for five days per week. In another alternative embodiment, the secondary component compound may be administered once per day each day of the week. In yet another alternative embodiment, the secondary component compound may be administered twice per day at least one day per week. Whenever the secondary component compound is administered on more than one day per week and less than seven days per week, the compound may be administered on consecutive days or non-consecutive days, as desired.

The methods of the present invention may be performed on any suitable subject. Suitable subjects include but are not limited to animals such as but not limited to humans, non-human primates, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

The IRM compounds used in the examples are identified in Table 1.

TABLE 1

IRM Compounds

| Compound | Chemical Name | Reference |
|---|---|---|
| IRM1 | 4-amino-α,α-dimethyl-2-ethoxymethyl-1H-imidazo[4,5-c]quinolin-1-ethanol | U.S. Pat. No. 5,389,640 Example 99 |
| IRM2 | 4-amino-α,α,2-trimethyl-1H-imidazo[4,5-c]quinoline-1-ethanol | U.S. Pat. No. 5,266,575 Example C1 |
| IRM3 | 1-(2-methylpropyl)-1H-imidazo[4,5-c]quinolin-4-amine | U.S. Pat. No. 4,689,338 Example 99 |
| IRM4 | 4-amino-α,α-dimethyl-1H-imidazo[4,5-c]quinoline-1-ethanol | U.S. Pat. No. 4,689,338 Example 189 |
| IRM5 | 4-amino-2-(ethoxymethyl)-α,α-dimethyl-6,7,8,9-tetrahydro-1H-imidazo[4,5-c]quinoline-1-ethanol | U.S. Pat. No. 5,352,784 Example 91 |
| IRM6 | 2-methyl-1-(2-methylpropyl)-1H-imidazo[4,5-c][1,5]naphthyridin-4-amine | U.S. Pat. No. 6,194,425 Example 36 |
| IRM7 | N-[4-(4-amino-2-butyl-1H-imidazo[4,5-c][1,5]naphthyridin-1-yl)butyl]-N'-cyclohexylurea | U.S. Pat. No. 6,194,425 Example 48 |
| IRM8 | N-[4-(4-amino-2-ethyl-1H-imidazo[4,5-c]quinolin-1-yl)butyl]methanesulfonamide | U.S. Pat. No. 6,677,349 Example 236 |
| IRM9 | N-[4-(4-amino-2-methyl-6,7,8,9,-tetrahydro-1H-imidazo[4,5-c]quinolin-1-yl)butyl]morpholine-4-carboxamide | U.S. Pat. No. 6,573,273 Example 170 |
| IRM10 | N-{2-[4-amino-2-(ethoxymethyl)-1H-imidazo[4,5-c]quinolin-1-yl]-1,1-dimethylethyl}methanesulfonamide | U.S. Pat. No. 6,677,349 Example 268 |

Example 1

Whole blood from healthy human donors was collected by venipuncture into EDTA vacutainer tubes (Becton Dickinson Labware, Lincoln Park, N.J.). Peripheral blood mononuclear cells (PBMCs) are separated from whole blood by density gradient centrifugation using HISTOPAQUE-1077 (Sigma-Aldrich Chemical Co., St. Louis, Mo.). The PBMCs are washed twice with Hank's Balanced Salts Solution (Celox Laboratories, Inc., Hopkins, Minn.) and then are suspended at $3-4 \times 10^6$ cells/mL in RPMI complete culture medium (Celox Laboratories, Inc., Hopkins, Minn.). The PBMC suspension was added to 48 well flat bottom sterile tissue culture plates (Becton Dickinson Labware, Lincoln Park, N.J.) containing an equal volume of RPMI complete media containing dexamethasone (Sigma Chemical Co., St. Louis, Mo.) at one of the dexamethasone concentrations indicated in Table 2.

After one hour, IRM1 was added to a final concentration of 1 µM, and then incubated at 37° C. for an additional 24 hours. Following incubation the cells were centrifuged for 5-10 minutes at 1000 rpm (~200×g) at 4° C. The cell-free culture supernatant is removed with a sterile polypropylene pipette and transferred to sterile polypropylene tubes. Samples were maintained at −70° C. until analysis.

The samples were analyzed for IFN-α and TNF-α secreted into the culture medium. The concentration of secreted IFN-α was determined by ELISA using a Human Multi-Species kit (PBL Biomedical Laboratories, Piscataway, N.J.). Secreted TNF-α was assayed by ELISA (R&D Systems, Minneapolis, Minn.). Results are shown in Table 2.

TABLE 2

| Treatment | TNF (pg/mL) | IFN (U/mL) |
|---|---|---|
| Medium | 0 | 0 |
| IRM1 (1 µM) | 3000 | 959 |
| IRM1 (1 µM) + dexamethasone (100 nM) | 156 | 421 |
| IRM1 (1 µM) + dexamethasone (10 nM) | 114 | 421 |

TABLE 2-continued

| Treatment | TNF (pg/mL) | IFN (U/mL) |
|---|---|---|
| IRM1 (1 µM) + dexamethasone (1.0 nM) | 247 | 185 |
| IRM1 (1 µM) + dexamethasone (0.1 nM) | 1260 | 185 |
| IRM1 (1 µM) + dexamethasone (0.01 nM) | 3000 | 421 |

Example 2

Human PBMCs were collected and prepared as described in Example 1. The cells were incubated in dexamethasone at one of the concentration indicated in Table 3. After one hour, the cells were treated with IRM compound, LPS, or left unstimulated, and then incubated for an additional 24 hours.

Secreted TNF-α was assayed by ELISA (Biosource International, Inc., Camarillo, Calif.). Results are expressed as pg/mL and are shown in Table 3.

TABLE 3

| Treatment | 0 µM Dex. | 0.01 µM Dex. | 0.1 µM Dex. | 1.0 µM Dex. |
|---|---|---|---|---|
| Medium | 0 | 0 | 45 | 0 |
| IRM2 (1.0 µg/mL) | 1570 | 775 | 224 | 191 |
| LPS (0.1 µg/mL) | 3300 | 1630 | 1620 | 874 |

Example 3

A dexamethasone solution was prepared in saline and administered orally (3 mg/kg) to male CFW mice (Charles River Laboratories, Inc., Wilmington, Mass.) once or once daily for five days. Thirty minutes after the final administration of dexamethasone, the mice were challenged with a solution of IRM2 prepared in saline to provide a dose of 10 mg/kg. The mice were bled either 2 hours or 3 hours after being challenged with IRM2. Serum samples were analyzed by for TNF by ELISA as described in Example 1. The results are expressed as pg/mL and are shown in Table 4.

TABLE 4

| Treatment | 2 hrs. post-challenge | 3 hrs. post-challenge |
|---|---|---|
| Unchallenged | 5.3 | * |
| IRM2 | 2983 | 487 |
| IRM2 + 1x dexamethasone | 1525 | 248 |
| IRM2 + 5x dexamethasone | 306 | 78 |

* not analyzed

Example 4

Human PBMCs were collected and prepared as described in Example 1. The cells were incubated with an anti-TNF monoclonal antibody (mouse anti-human TNF, Promega Corp., Madison, Wis.). After one hour, the cells were treated with IRM compound, LPS, or left unstimulated, and then incubated for an additional 24 hours.

Secreted TNF-α and IL-6 were assayed by ELISA (Biosource International, Inc., Camarillo, Calif.). Results are expressed in pg/mL for each cytokine.

Secreted IFN was assayed using a virus neutralization bioassay using A549 human lung carcinoma cells challenged with encephalomyocarditis. The details of the bioassay method have been described by G. L. Brennan and L. H. Kronenberg in "Automated Bioassay of Interferons in Microtest Plates", Biotechniques, Jun./Jul. 78, 1983, incorporated herein by reference. Briefly stated the method is as follows: A549 cells are incubated with dilutions of samples or a standard interferon at 37° C. for 24 hours. The incubated cells are then infected with an inoculum of encephalomyocarditis virus. The infected cells are incubated for an additional 24 hours at 37° C. before evaluating for viral cytopathic effect. The viral cytopathic effect is quantified by staining with crystal violet followed by visual scoring of the plates. Results are expressed as alpha reference units/mL based on the value obtained for NIH Human Leukocyte IFN standard.

Results are shown in Table 5.

TABLE 5

| | TNF (pg/mL) | | IL-6 (pg/mL) | | IFN (U/mL) | |
|---|---|---|---|---|---|---|
| Treatment | No Ab | +Ab | No Ab | +Ab | No Ab | +Ab |
| Medium | 5 | 0 | 0 | 702 | 0 | 0 |
| IRM2 (1.0 μg/mL) | 1340 | 61 | 20137 | 24189 | 460 | 290 |
| LPS (0.1 μg/mL) | 1060 | 61 | 22979 | 26111 | 22 | 8.8 |

Example 5

Human PBMCs are collected and prepared as described in Example 1. After one hour, IRM3, IRM4, IRM5, IRM6, IRM7, IRM8, IRM9, or IRM10 is added to a final concentration of 1 μM, and then incubated at 37° C. for an additional 24 hours. The samples are analyzed for IFN-α and TNF-α as described in Example 1. Results will show inhibition of IRM-induced TNF-α by dexamethasone in a dose dependent manner.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of treating neoplastic tumors, comprising administering to a subject having the neoplastic tumors a therapeutic combination that comprises
   (a) an IRM compound agonist of at least one of TLR7 or TLR8 in an amount effective to treat the neoplastic tumors, where the IRM compound comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine; and
   (b) an anti-inflammatory compound in an amount effective to limit a side effect of administering the IRM compound, wherein the anti-inflammatory compound comprises a glucocorticoid.

2. The method of claim 1 wherein the IRM compound and the anti-inflammatory compound are administered at different sites.

3. The method of claim 1 wherein the IRM compound and the anti-inflammatory compound are administered at different times.

4. The method of claim 1, wherein the IRM compound is other than 1-(2-methylpropyl)-1H-imidazo[4,5-c]quinolin-4-amine.

5. The method of claim 1, wherein the imidazoquinoline amine is a amide substituted imidazoquinoline amine, sulfonamide substituted imidazoquinoline amine, urea substituted imidazoquinoline amine, aryl ether substituted imidazoquinoline amine, heterocyclic ether substituted imidazoquinoline amine, amido ether substituted imidazoquinoline amine, sulfonamido ether substituted imidazoquinoline amine, urea substituted imidazoquinoline ether, thioether substituted imidazoquinoline amine, or a 6-, 7-, 8-, or 9-aryl, heteroaryl, aryloxy or arylalkyleneoxy substituted imidazoquinoline amine.

6. The method of claim 1, wherein the neoplastic tumors are from basal cell carcinoma or actinic keratosis.

7. A method of treating neoplastic tumors, comprising administering to a subject having the neoplastic tumors a therapeutic combination that comprises
   (a) an IRM compound agonist of at least one of TLR7 or TLR8 in an amount effective to treat the neoplastic tumors, where the IRM compound comprises a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine; and
   (b) an anti-inflammatory compound in an amount effective to limit a side effect of administering the IRM compound, wherein the substituted imidazoquinoline amine is a amide substituted imidazoquinoline amine, sulfonamide substituted imidazoquinoline amine, urea substituted imidazoquinoline amine, aryl ether substituted imidazoquinoline amine, heterocyclic ether substituted imidazoquinoline amine, amido ether substituted imidazoquinoline amine, sulfonamido ether substituted imidazoquinoline amine, urea substituted imidazoquinoline ether, thioether substituted imidazoquinoline amine, or a 6-, 7-, 8-, or 9-aryl, heteroaryl, aryloxy or arylalkyleneoxy substituted imidazoquinoline amine.

8. The method of claim 7, wherein the IRM compound and the anti-inflammatory compound are administered at different sites.

9. The method of claim 7, wherein the IRM compound and the anti-inflammatory compound are administered at different times.

10. The method of claim 7, wherein the neoplastic tumors are from basal cell carcinoma or actinic keratosis.

11. A method of treating warts, basal cell carcinoma or actinic keratosis, comprising administering to a subject having the warts, basal cell carcinoma or actinic keratosis a therapeutic combination that comprises (a) an IRM compound agonist of at least one of TLR7 or TLR8 in an amount effective to treat the warts, basal cell carcinoma or actinic keratosis, where the IRM compound comprises an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine; and (b) an anti-inflammatory compound in an amount effective to limit a side effect of administering the IRM compound.

12. The method of claim 11, wherein the IRM compound and the anti-inflammatory compound are administered at different sites.

13. The method of claim 11, wherein the IRM compound and the anti-inflammatory compound are administered at different times.

* * * * *

UNITED STATES PATENT AND TRADEMARK OFFICE
CERTIFICATE OF CORRECTION

PATENT NO. : 8,940,755 B2  
APPLICATION NO. : 11/001979  
DATED : January 27, 2015  
INVENTOR(S) : Tomai et al.

Page 1 of 1

It is certified that error appears in the above-identified patent and that said Letters Patent is hereby corrected as shown below:

On the title page item [56]

Page 2 Col. 2 (Other Publications)
Line 27, delete "Bioorgianic" and insert -- Bioorganic --, therefor.

Line 63, delete "sythesis:" and insert -- synthesis: --, therefor.

In the specification

Column 1
Line 21, delete "usefill" and insert -- useful --, therefor.

Column 3
Line 32, delete "Aspergillis fumigatus., Candida albicans.," and insert
-- Aspergillus fumigatus, Candida albicans, --, therefor.

Column 8
Line 4, delete "amcidonide," and insert -- amcinonide, --, therefor.

Line 7, delete "diflucotolone," and insert -- diflucortolone, --, therefor.

Lines 26-27, delete "acetretin" and insert -- acitretin, --, therefor.

Line 30, delete "mycophenalate," and insert -- mycophenolate, --, therefor.

Column 9
Line 48, delete "Aspergillis" and insert -- Aspergillus --, therefor.

Signed and Sealed this  
Third Day of November, 2015

Michelle K. Lee  
*Director of the United States Patent and Trademark Office*